United States Patent
Jehan et al.

(10) Patent No.: US 9,536,560 B2
(45) Date of Patent: Jan. 3, 2017

(54) CADENCE DETERMINATION AND MEDIA CONTENT SELECTION

(71) Applicant: Spotify AB, Stockholm (SE)

(72) Inventors: Tristan Jehan, Brooklyn, NY (US); Sten Garmark, Stockholm (SE); Dariusz Dziuk, Stockholm (SE); Rahul Sen, Stockholm (SE); Owen Smith, Stockholm (SE); Lars Christian Olofsson, Hägersten (SE); Nikolaos Toumpelis, Stockholm (SE)

(73) Assignee: Spotify AB, Stockholm (SE)

( * ) Notice: Subject to any disclaimer, the term of this patent is extended or adjusted under 35 U.S.C. 154(b) by 0 days.

(21) Appl. No.: 14/883,232

(22) Filed: Oct. 14, 2015

(65) Prior Publication Data
US 2016/0343399 A1  Nov. 24, 2016

Related U.S. Application Data

(60) Provisional application No. 62/163,840, filed on May 19, 2015.

(51) Int. Cl.
| | |
|---|---|
| *G06F 17/00* | (2006.01) |
| *G11B 20/10* | (2006.01) |
| *G10H 1/00* | (2006.01) |
| *A61B 5/11* | (2006.01) |
| *A61B 5/00* | (2006.01) |

(52) U.S. Cl.
CPC ........ *G11B 20/10527* (2013.01); *A61B 5/1118* (2013.01); *A61B 5/742* (2013.01); *A61B 5/7405* (2013.01); *G10H 1/0008* (2013.01); *A61B 2503/12* (2013.01); *A61B 2562/0219* (2013.01); *G10H 2210/076* (2013.01)

(58) Field of Classification Search
CPC .............. G10H 2210/076; G10H 2210/391; G10H 2220/371; G10H 2240/131; A63B 71/0686; A63B 2071/0625
See application file for complete search history.

(56) References Cited

U.S. PATENT DOCUMENTS

| | | |
|---|---|---|
| 7,767,897 B2 | 8/2010 | Jochelson et al. |
| 8,738,925 B1 | 5/2014 | Park et al. |
| (Continued) | | |

OTHER PUBLICATIONS

U.S. Appl. No. 14/883,252, filed Oct. 14, 2015 for "Repetitive Motion Activity Enhancement Based Upon Media Content Selection".

(Continued)

*Primary Examiner* — Joseph Saunders, Jr.
(74) *Attorney, Agent, or Firm* — Merchant & Gould P.C.

(57) ABSTRACT

Systems, devices, apparatuses, components, methods, and techniques for cadence determination and media content selection are provided. An example media-playback device comprises a media-output device that plays media content items, a cadence-acquiring device, and a cadence-based media content selection engine. The cadence-acquiring device includes an accelerometer and a cadence-determination engine configured to determine a cadence based on acceleration data captured by the accelerometer. The cadence-based media content selection engine is configured to identify a media content item based on the cadence determined by the cadence-determining engine and cause the media-output device to playback the identified media content item.

16 Claims, 11 Drawing Sheets

(56) References Cited

U.S. PATENT DOCUMENTS

| | | |
|---|---|---|
| 8,932,218 B1 | 1/2015 | Thompson |
| 2002/0093841 A1 | 7/2002 | Kitayama et al. |
| 2002/0107649 A1 | 8/2002 | Takiguchi et al. |
| 2002/0172379 A1 | 11/2002 | Cliff |
| 2004/0122662 A1 | 6/2004 | Crockett |
| 2005/0286213 A1 | 12/2005 | Rooney |
| 2006/0000344 A1 | 1/2006 | Basu |
| 2006/0107822 A1 | 5/2006 | Bowen |
| 2007/0137464 A1 | 6/2007 | Moulios et al. |
| 2007/0240558 A1 | 10/2007 | Seppanen et al. |
| 2007/0254271 A1 | 11/2007 | Burlik et al. |
| 2007/0261537 A1 | 11/2007 | Eronen et al. |
| 2008/0096726 A1 | 4/2008 | Riley et al. |
| 2008/0097633 A1 | 4/2008 | Jochelson et al. |
| 2008/0153671 A1 | 6/2008 | Ogg et al. |
| 2008/0314232 A1 | 12/2008 | Hansson et al. |
| 2009/0319221 A1* | 12/2009 | Kahn .............. A61B 5/1123 702/141 |
| 2010/0030085 A1 | 2/2010 | Rojas Ojeda et al. |
| 2011/0153042 A1 | 6/2011 | Burton et al. |
| 2012/0059494 A1 | 3/2012 | David |
| 2012/0136573 A1 | 5/2012 | Janardhanan et al. |
| 2013/0171599 A1 | 7/2013 | Bleich et al. |
| 2013/0179112 A1 | 7/2013 | Ma et al. |
| 2013/0190903 A1 | 7/2013 | Balakrishnan et al. |
| 2013/0312589 A1* | 11/2013 | MacPherson ............ G10H 1/42 84/612 |
| 2014/0213920 A1 | 7/2014 | Lee et al. |
| 2015/0080746 A1 | 3/2015 | Bleich et al. |
| 2015/0142147 A1 | 5/2015 | Stanghed et al. |
| 2015/0182149 A1 | 7/2015 | Rapoport et al. |
| 2016/0093107 A1 | 3/2016 | Yamamoto et al. |

OTHER PUBLICATIONS

U.S. Appl. No. 14/883,245, filed Oct. 14, 2015 for "Heart Rate Control Based Upon Media Content Selection".

U.S. Appl. No. 14/883,298, filed Oct. 14, 2015 for "Cadence-Based Playlists Management System".

U.S. Appl. No. 14/883,273, filed Oct. 14, 2015 for "Multi-Track Playback of Media content During Repetitive Motion Activities".

U.S. Appl. No. 14/883,295, filed Oct. 14, 2015 for "Search Media Content Based Upon Tempo".

U.S. Appl. No. 14/883,318, filed Oct. 14, 2015 for "Cadence and Media Content Phase Alignment".

U.S. Appl. No. 14/944,972, filed Nov. 18, 2015 for "System for Managing Transitions Between Media Content Items".

U.S. Appl. No. 14/945,008, filed Nov. 18, 2015 for "Identifying Media Content".

U.S. Appl. No. 14/883,323, filed Oct. 14, 2015 for "Accessibility Management System for Media Content Items".

U.S. Appl. No. 14/883,336, filed Oct. 14, 2015 for "Selection and Playback of Song Versions Using Cadence".

U.S. Appl. No. 14/883,340, filed Oct. 14, 2015 for "Cadence-Based Selection, Playback, and Transition Between Song Versions".

* cited by examiner

CADENCE DETERMINATION AND MEDIA CONTENT SELECTION

CROSS-REFERENCE TO RELATED APPLICATION

This application claims priority to U.S. Ser. No. 62/163,840, filed May 19, 2015 entitled CADENCE DETERMINATION AND MEDIA CONTENT SELECTION, the disclosure of which is hereby incorporated by reference in its entirety.

BACKGROUND

Running, as well as many other recreation or fitness activities, include repetitive motions. For example, running and walking involve repetitive steps, biking involves repetitive rotational movements, rowing involves repetitive strokes, and swimming involves repetitive strokes and kicks. There are of course many other recreation and fitness activities that also include various repetitive motions. These repetitive motion activities may be performed in place (e.g., using a treadmill, stationary bike, rowing machine, swimming machine, etc.) or in motion (e.g., on roads, trails, or tracks or in a pool or body of water, etc.). Cadence refers to the frequency of these repetitive motions and is often measured in terms of motions per minute (e.g., steps per minute, rotations per minute, strokes per minute, or kicks per minute).

Many people enjoy consuming media content, such as listening to audio content or watching video content, while running or engaging in other repetitive-motion activities. Examples of audio content include songs, albums, podcasts, audiobooks, etc. Examples of video content include movies, music videos, television episodes, etc. Using a mobile phone or other media-playback device a person can access large catalogs of media content. For example, a user can access an almost limitless catalog of media content through various free and subscription-based streaming services. Additionally, a user can store a large catalog of media content on his or her mobile device.

This nearly limitless access to media content introduces new challenges for users. For example, it may be difficult to find or select the right media content that complements a particular moment during a run or other repetitive-motion activity.

SUMMARY

In general terms, this disclosure is directed to cadence determination and media content selection. In one possible configuration and by non-limiting example, a media-playback device acquires a cadence associated with a repetitive-motion activity that the user is engaging in and selects media content items based on that acquired cadence. Various aspects are described in this disclosure, which include, but are not limited to, the following aspects.

In a first aspect, a media-playback device comprising: a media-output device that plays media content items; a cadence-acquiring device comprising an accelerometer and a cadence-determination engine configured to determine a cadence based on acceleration data captured by the accelerometer; and a cadence-based media content selection engine configured to: identify a media content item based on the cadence determined by the cadence-determining engine; and cause the media-output device to playback the identified media content item.

In another aspect, a method of cadence-based media playback for use during repetitive-motion activities comprising: determining a cadence associated with a repetitive motion activity based on acceleration data captured by a plurality of accelerometers, wherein the acceleration data comprises sequences of acceleration sample data captured from each of the plurality of accelerometers over a duration of time; identifying a media content item based on the determined cadence; and playing back the identified media content item.

In yet another aspect, a method of cadence-based media playback for use during repetitive-motion activities comprising: capturing acceleration data by a plurality of accelerometers over a duration of time, wherein the acceleration data comprises sequences of acceleration measurements captured at particular times throughout the duration by each of the accelerometers; filtering each of the sequences of measurements based on frequency to generate filtered sequences; identifying a cadence signal corresponding to the cadence from the filtered sequences, wherein the signal corresponding to the cadence is identified by combining the filtered sequences having the highest energy during subintervals of the duration; calculating a sequence of aggregate values corresponding to periods of oscillation of the cadence signal over intervals during the duration of time; smoothing the sequence of aggregate values to generate a sequence of second aggregate values; determining whether the sequence of aggregate values and the sequence of second aggregate values satisfy predetermined tolerances, wherein the predetermined tolerances include a difference tolerance and a duration requirement; and upon determining that the predetermined tolerances are satisfied, calculating an initial cadence value based on the sequence of aggregate values.

DETAILED DESCRIPTION

Figure 1:
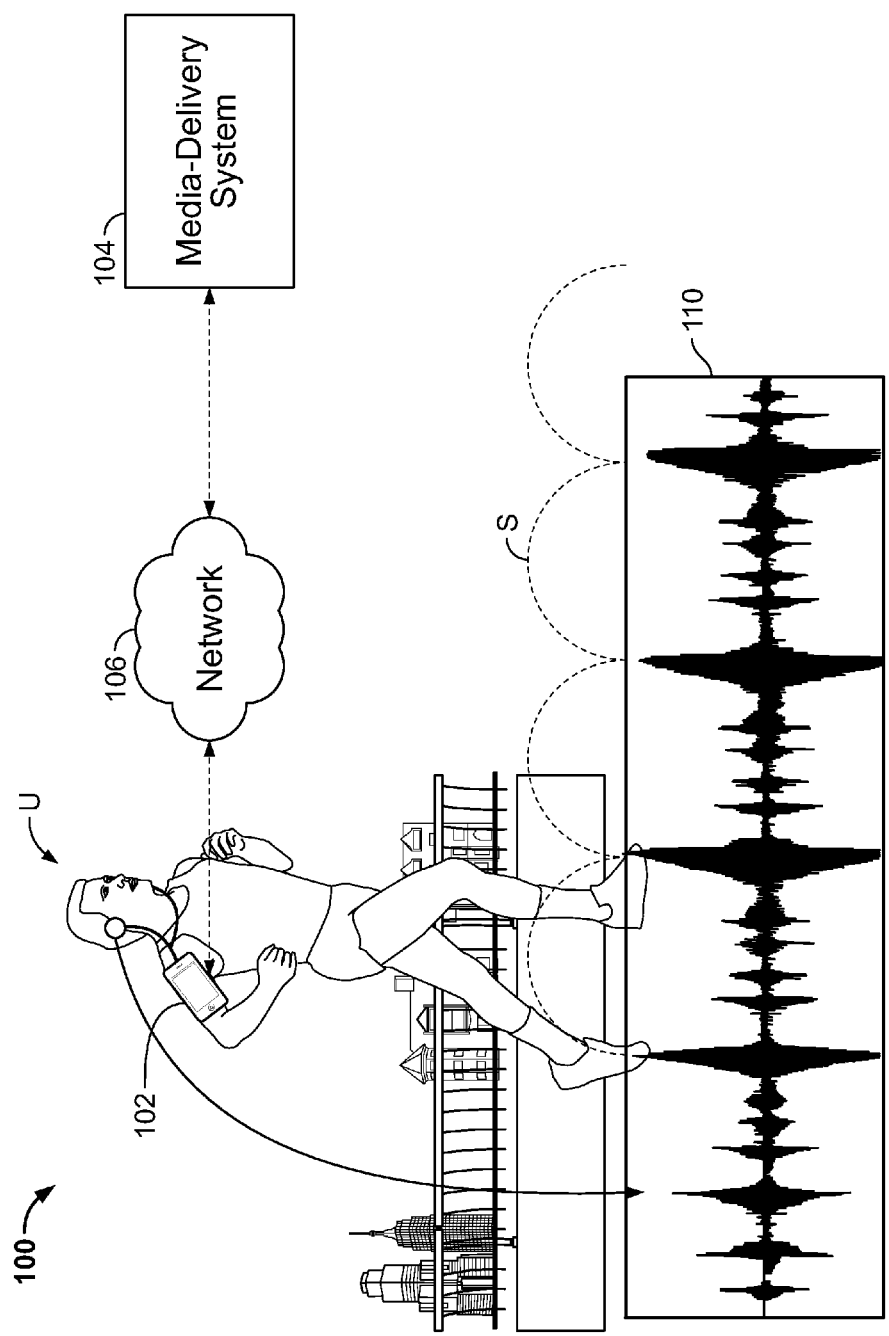
FIG. 1 illustrates an example system for cadence determination and media content selection.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Users of media-playback devices often consume media content while engaging in various activities, including repetitive motion activities. As noted above, examples of repetitive-motion activities may include swimming, biking, running, rowing, and other activities. Consuming media content may include one or more of listening to audio content, watching video content, or consuming other types of media content. For ease of explanation, the embodiments described in this application are presented using specific examples. For example, audio content (and in particular music) is described as an example of one form of media consumption. As another example, running is described as one example of a repetitive-motion activity. However, it should be understood that the same concepts are equally applicable to other forms of media consumption and to other forms of repetitive-motion activities, and at least some embodiments include other forms of media consumption and/or other forms of repetitive-motion activities.

The users may desire that the media content fits well with the particular repetitive-motion activity. For example, a user who is running may desire to listen to music with a beat that corresponds to the user's cadence. Beneficially, by matching the beat of the music to the cadence, the user's performance or enjoyment of the repetitive-motion activity may be enhanced. This desire cannot be met with traditional media-playback devices and media-delivery systems.

FIG. 1 illustrates an example system 100 for cadence determination and media content selection. The example system 100 includes a media-playback device 102 and a media-delivery system 104. The system 100 communicates across a network 106. Also shown, is a user U who is running. The user U's upcoming steps S are shown as well. A step represents a single strike of the runner's foot upon the ground.

The media-playback device 102 operates to play media content items to produce media output 110. In some embodiments, the media content items are provided by the media-delivery system 104 and transmitted to the media-playback device 102 using the network 106. A media content item is an item of media content, including audio, video, or other types of media content, which may be stored in any format suitable for storing media content. Non-limiting examples of media content items include songs, albums, music videos, movies, television episodes, podcasts, other types of audio or video content, and portions or combinations thereof.

The media-playback device 102 plays media content for the user based on the user's cadence. In the example shown, the media output 110 includes music with a tempo that corresponds to the user's cadence. The tempo (or rhythm) of music refers to the frequency of the beat and is typically measured in beats per minute (BPM). The beat is the basic unit of rhythm in a musical composition (as determined by the time signature of the music). Accordingly, in the example shown, the user U's steps occur at the same frequency as the beat of the music.

For example, if the user U is running at a cadence of 180 steps per minute, the media-playback device 102 may play a media content item having a tempo equal to or approximately equal to 180 BPM. In other embodiments, the media-playback device 102 plays a media content item having a tempo equal or approximately equal to the result of dividing the cadence by an integer such as a tempo that is equal to or approximately equal to one-half (e.g., 90 BPM when the user is running at a cadence of 180 steps per minute), one-fourth, or one-eighth of the cadence. Alternatively, the media-playback device 102 plays a media content item having a tempo that is equal or approximately equal to an integer multiple (e.g., 2×, 4×, etc.) of the cadence. Further, in some embodiments, the media-playback device 102 operates to play multiple media content items including one or more media content items having a tempo equal to or approximately equal to the cadence and one or more media content items have a tempo equal or approximately equal to the result of multiplying or dividing the cadence by an integer. Various other combinations are possible as well.

In some embodiments, the media-playback device 102 operates to play music having a tempo that is within a predetermined range of a target tempo. In at least some embodiments, the predetermined range is plus or minus 2.5 BPM. For example, if the user U is running at a cadence of 180 steps per minute, the media-playback device 102 operates to play music having a tempo of 177.5-182.5 BPM. Alternatively, in other embodiments, the predetermined range is itself in a range from 1 BPM to 10 BPM.

Further, in some embodiments, the media-playback device 102 operates to play music having a tempo equal to or approximately equal to a user U's cadence after it is rounded. For example, the cadence may be rounded to the nearest multiple of 2.5, 5, or 10 and then the media-playback device 102 plays music having a tempo equal to or approximately equal to the rounded cadence. In yet other embodiments, the media-playback device 102 uses the cadence to select a predetermined tempo range of music for playback. For example, if the user U's cadence is 181 steps per minute, the media-playback device 102 may operate to play music from a predetermined tempo range of 180-184.9 BPM; while if the user U's cadence is 178 steps per minute, the media-playback device 102 may operate to play music from a predetermined tempo range of 175-179.9 BPM.

Figure 2:
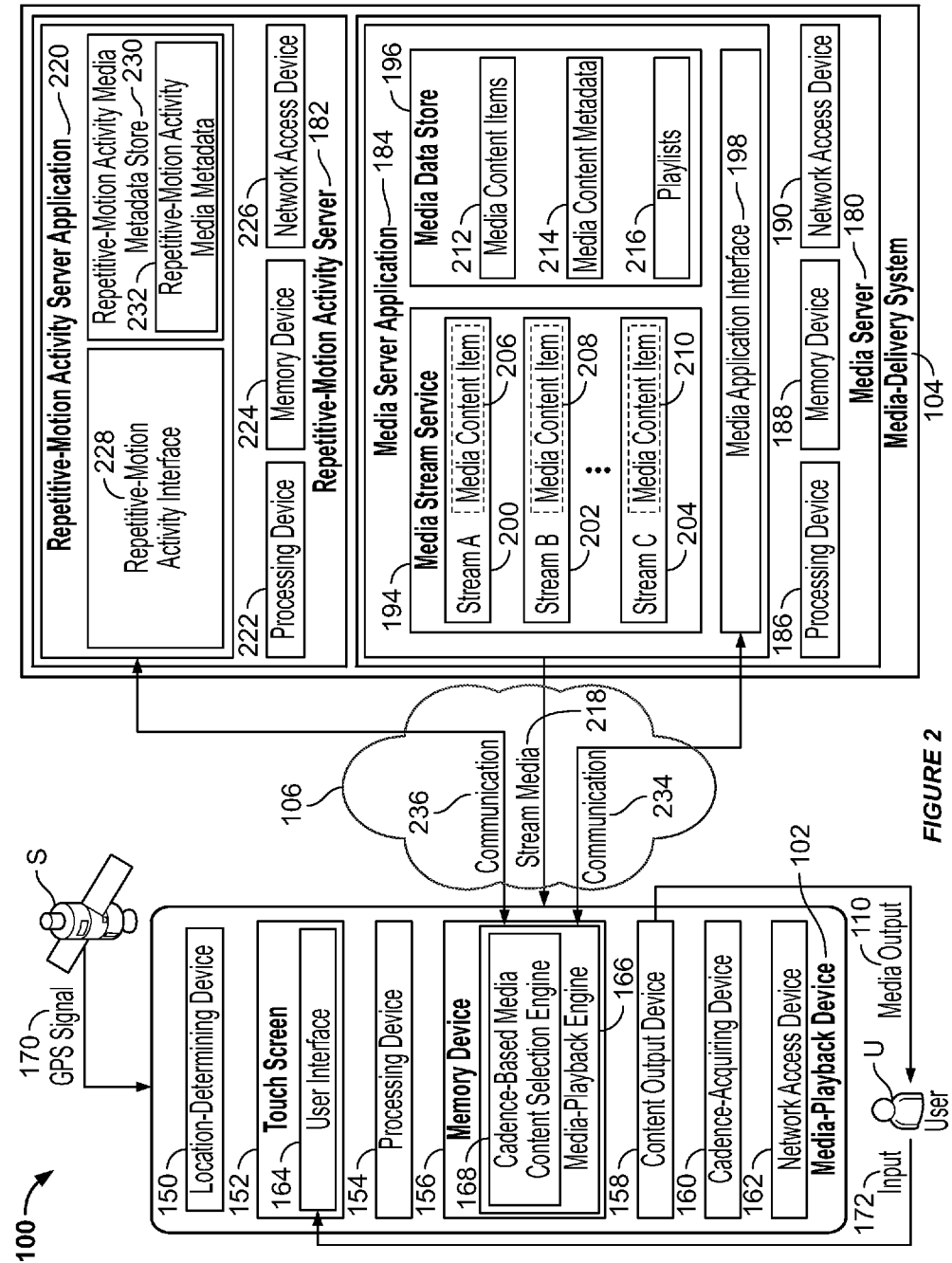
FIG. 2 is a schematic illustration of the example system of FIG. 1.

FIG. 2 is a schematic illustration of an example system 100 for cadence determination and media content selection. In FIG. 2, the media-playback device 102, the media-delivery system 104, and the network 106 are shown. Also shown are the user U and a satellite S.

As noted above, the media-playback device 102 operates to play media content items. In some embodiments, the media-playback device 102 operates to play media content items that are provided (e.g., streamed, transmitted, etc.) by a system external to the media-playback device such as the media-delivery system 104, another system, or a peer device. Alternatively, in some embodiments, the media-playback device 102 operates to play media content items stored locally on the media-playback device 102. Further, in at least some embodiments, the media-playback device 102 operates to play media content items that are stored locally as well as media content items provided by other systems.

In some embodiments, the media-playback device 102 is a computing device, handheld entertainment device, smartphone, tablet, watch, wearable device, or any other type of device capable of playing media content. In yet other embodiments, the media-playback device 102 is a laptop computer, desktop computer, television, gaming console, set-top box, network appliance, blue-ray or DVD player, media player, stereo, or radio.

In at least some embodiments, the media-playback device 102 includes a location-determining device 150, a touch screen 152, a processing device 154, a memory device 156, a content output device 158, a cadence-acquiring device 160, and a network access device 162. Other embodiments may include additional, different, or fewer components. For example, some embodiments may include a recording device such as a microphone or camera that operates to record audio or video content. As another example, some embodiments do not include one or more of the location-determining device 150 and the touch screen 152.

The location-determining device 150 is a device that determines the location of the media-playback device 102. In some embodiments, the location-determining device 150 uses one or more of the following technologies: Global Positioning System (GPS) technology which may receive GPS signals 170 from satellites S, cellular triangulation technology, network-based location identification technology, Wi-Fi positioning systems technology, and combinations thereof.

The touch screen 152 operates to receive an input 172 from a selector (e.g., a finger, stylus etc.) controlled by the user U. In some embodiments, the touch screen 152 operates as both a display device and a user input device. In some embodiments, the touch screen 152 detects inputs based on one or both of touches and near-touches. In some embodiments, the touch screen 152 displays a user interface 164 for interacting with the media-playback device 102. As noted above, some embodiments do not include a touch screen 152. Some embodiments include a display device and one or more separate user interface devices. Further, some embodiments do not include a display device.

In some embodiments, the processing device 154 comprises one or more central processing units (CPU). In other embodiments, the processing device 154 additionally or alternatively includes one or more digital signal processors, field-programmable gate arrays, or other electronic circuits.

The memory device 156 operates to store data and instructions. In some embodiments, the memory device 156 stores instructions for a media-playback engine 166 that includes a cadence-based media content selection engine 168. In some embodiments, the media-playback engine 166 operates to playback media content and the cadence-based media content selection engine 168 operates to select media content for playback based on a cadence.

The memory device 156 typically includes at least some form of computer-readable media. Computer readable media includes any available media that can be accessed by the media-playback device 102. By way of example, computer-readable media include computer readable storage media and computer readable communication media.

Computer readable storage media includes volatile and nonvolatile, removable and non-removable media implemented in any device configured to store information such as computer readable instructions, data structures, program modules, or other data. Computer readable storage media includes, but is not limited to, random access memory, read only memory, electrically erasable programmable read only memory, flash memory and other memory technology, compact disc read only memory, blue ray discs, digital versatile discs or other optical storage, magnetic cassettes, magnetic tape, magnetic disk storage or other magnetic storage devices, or any other medium that can be used to store the desired information and that can be accessed by the media-playback device 102. In some embodiments, computer readable storage media is non-transitory computer readable storage media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The content output device 158 operates to output media content. In some embodiments, the content output device 158 generates media output 110 for the user U. Examples of the content output device 158 include a speaker, an audio output jack, a Bluetooth transmitter, a display panel, and a video output jack. Other embodiments are possible as well. For example, the content output device 158 may transmit a signal through the audio output jack or Bluetooth transmitter that can be used to reproduce an audio signal by a connected or paired device such as headphones or a speaker.

The cadence-acquiring device 160 operates to acquire a cadence associated with the user U. In at least some embodiments, the cadence-acquiring device 160 operates to determine cadence directly and includes one or more accelerometers or other motion-detecting technologies. Alternatively, the cadence-acquiring device 160 operates to receive data representing a cadence associated with the user U. For example, in some embodiments, the cadence-acquiring device 160 operates to receive data from a watch, bracelet, foot pod, chest strap, shoe insert, anklet, smart sock, bicycle computer, exercise equipment (e.g., treadmill, rowing machine, stationary cycle), or other device for determining or measuring cadence. Further, in some embodiments, the cadence-acquiring device 160 operates to receive a cadence value input by the user U or another person.

The network access device 162 operates to communicate with other computing devices over one or more networks, such as the network 106. Examples of the network access device include wired network interfaces and wireless network interfaces. Wireless network interfaces includes infrared, BLUETOOTH® wireless technology, 802.11a/b/g/n/ac, and cellular or other radio frequency interfaces in at least some possible embodiments.

The network 106 is an electronic communication network that facilitates communication between the media-playback device 102 and the media-delivery system 104. An electronic communication network includes a set of computing devices and links between the computing devices. The computing devices in the network use the links to enable communication among the computing devices in the network. The network 106 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 106 includes various types of links. For example, the network 106 can include wired and/or wireless links, including Bluetooth, ultra-wideband (UWB), 802.11, ZigBee, cellular, and other types of wireless links. Furthermore, in various embodiments, the network 106 is implemented at various scales. For example, the network 106 can be implemented as one or more local area networks (LANs), metropolitan area networks, subnets, wide area networks (such as the Internet), or can be implemented at another scale. Further, in some embodiments, the network 106 includes multiple networks, which may be of the same type or of multiple different types.

The media-delivery system 104 comprises one or more computing devices and operates to provide media content items to the media-playback devices 102 and, in some embodiments, other media-playback devices as well. The media-delivery system 104 includes a media server 180 and a repetitive-motion activity server 182. In at least some embodiments, the media server 180 and the repetitive-motion activity server 182 are provided by separate computing devices. In other embodiments, the media server 180 and the repetitive-motion activity server 182 are provided by the same computing devices. Further, in some embodiments, one or both of the media server 180 and the repetitive-motion activity server 182 are provided by multiple computing devices. For example, the media server 180 and the repetitive-motion activity server 182 may be provided by multiple redundant servers located in multiple geographic locations.

The media server 180 operates to transmit stream media 218 to media-playback devices such as the media-playback device 102. In some embodiments, the media server 180 includes a media server application 184, a processing device 186, a memory device 188, and a network access device 190. The processing device 186, memory device 188, and network access device 190 may be similar to the processing device 154, memory device 156, and network access device 162 respectively, which have each been previously described.

In some embodiments, the media server application 184 operates to stream music or other audio, video, or other forms of media content. The media server application 184 includes a media stream service 194, a media data store 196, and a media application interface 198. The media stream service 194 operates to buffer media content such as media content items 206, 208, and 210, for streaming to one or more streams 200, 202, and 204.

The media application interface 198 can receive requests or other communication from media-playback devices or other systems, to retrieve media content items from the media server 180. For example, in FIG. 2, the media application interface 198 receives communication 234 from the media-playback engine 166.

In some embodiments, the media data store 196 stores media content items 212, media content metadata 214, and playlists 216. The media data store 196 may comprise one or more databases and file systems. Other embodiments are possible as well. As noted above, the media content items 212 may be audio, video, or any other type of media content, which may be stored in any format for storing media content.

The media content metadata 214 operates to provide various information associated with the media content items 212. In some embodiments, the media content metadata 214 includes one or more of title, artist name, album name, length, genre, mood, era, etc. The playlists 216 operate to identify one or more of the media content items 212 and. In some embodiments, the playlists 216 identify a group of the media content items 212 in a particular order. In other embodiments, the playlists 216 merely identify a group of the media content items 212 without specifying a particular order. Some, but not necessarily all, of the media content items 212 included in a particular one of the playlists 216 are associated with a common characteristic such as a common genre, mood, or era.

The repetitive-motion activity server 182 operates to provide repetitive-motion activity-specific information about media content items to media-playback devices. In some embodiments, the repetitive-motion activity server 182 includes a repetitive-motion activity server application 220, a processing device 222, a memory device 224, and a network access device 226. The processing device 222, memory device 224, and network access device 226 may be similar to the processing device 154, memory device 156, and network access device 162 respectively, which have each been previously described.

In some embodiments, repetitive-motion activity server application 220 operates to transmit information about the suitability of one or more media content items for playback during a particular repetitive-motion activity. The repetitive-motion activity server application 220 includes a repetitive-motion activity interface 228 and a repetitive-motion activity media metadata store 230.

In some embodiments, the repetitive-motion activity server application 220 may provide a list of media content items at a particular tempo to a media-playback device in response to a request that includes a particular cadence value. Further, in some embodiments, the media content items included in the returned list will be particularly relevant for the repetitive motion activity in which the user is engaged (for example, if the user is running, the returned list of media content items may include only media content items that have been identified as being highly runnable).

The repetitive-motion activity interface 228 operates to receive requests or other communication from media-playback devices or other systems to retrieve information about media content items from the repetitive-motion activity server 182. For example, in FIG. 2, the repetitive-motion activity interface 228 receives communication 236 from the media-playback engine 166.

In some embodiments, the repetitive-motion activity media metadata store 230 stores repetitive-motion activity media metadata 232. The repetitive-motion activity media metadata store 230 may comprise one or more databases and file systems. Other embodiments are possible as well.

The repetitive-motion activity media metadata 232 operates to provide various information associated with media content items, such as the media content items 212. In some embodiments, the repetitive-motion activity media metadata 232 provides information that may be useful for selecting media content items for playback during a repetitive-motion activity. For example, in some embodiments, the repetitive-motion activity media metadata 232 stores runnability scores for media content items that correspond to the suitability of particular media content items for playback during running. As another example, in some embodiments, the repetitive-motion activity media metadata 232 stores timestamps (e.g., start and end points) that identify portions of a media content items that are particularly well-suited for playback during running (or another repetitive-motion activity).

Each of the media-playback device 102 and the media-delivery system 104 can include additional physical computer or hardware resources. In at least some embodiments, the media-playback device 102 communicates with the media-delivery system 104 via the network 106.

Although in FIG. 2 only a single media-playback device 102 and media-delivery system 104 are shown, in accordance with some embodiments, the media-delivery system 104 can support the simultaneous use of multiple media-playback devices, and the media-playback device can simultaneously access media content from multiple media-delivery systems. Additionally, although FIG. 2 illustrates a streaming media based system for cadence determination and media content selection, other embodiments are possible as well. For example, in some embodiments, the media-playback device 102 includes a media data store 196 and the media-playback device 102 is configured to perform cadence determination and media content selection without accessing the media-delivery system 104. Further in some embodiments, the media-playback device 102 operates to store previously streamed media content items in a local media data store.

In at least some embodiments, the media-delivery system 104 can be used to stream, progressively download, or otherwise communicate music, other audio, video, or other forms of media content items to the media-playback device 102 based on a cadence acquired by the cadence-acquiring device 160 of the media-playback device 102. In accordance with an embodiment, a user U can direct the input 172 to the user interface 164 to issue requests, for example, to playback media content corresponding to the cadence of a repetitive motion activity on the media-playback device 102.

Figure 3:
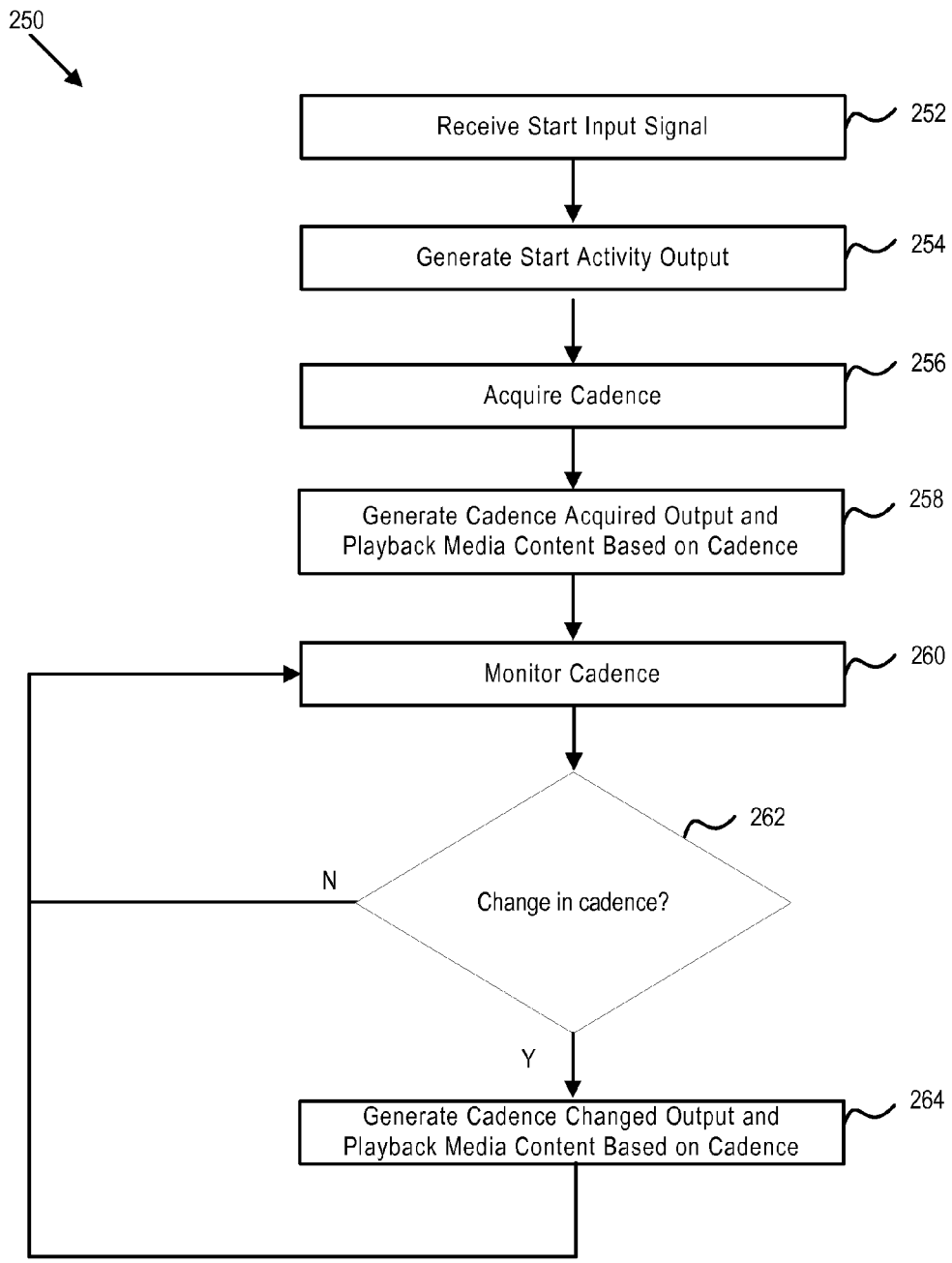
FIG. 3 illustrates an example method of cadence monitoring and media content selection performed by some embodiments of the media-playback device of FIG. 1.

FIG. 3 illustrates an example method 250 of cadence monitoring and media content selection performed by some embodiments of the media-playback device 102.

At operation 252, a start input signal is received by the media-playback device 102. Various embodiments operate to receive various start input signals. Example start input signals include a touch input from a selector on a particular location on the user interface 164 (e.g., a start button), a spoken command captured by a microphone or otherwise, or a movement that is detected by the media-playback device 102 such as the user beginning to run while holding the media-playback device 102.

At operation 254, a start activity output is generated. Various embodiments generate one or more start activity outputs. Examples of start activity outputs include generation of audible signals such as beeps, bells, sound effects, pre-recorded voiceovers (e.g., "Go," "Start Running," or "Start Activity"), etc. Other examples of start activity outputs include visual indicators on the user interface 164.

At operation 256, a cadence associated with a repetitive-motion activity of the user is acquired. In some embodiments, the cadence is acquired by determining the cadence based on movements of the media-playback device 102 (e.g., using the methods illustrated and described with respect to at least FIGS. 4-7). In other embodiments, the cadence is acquired from a separate device, from a user input, or otherwise. Regardless of how the cadence is acquired, once that cadence is acquired, the method 250 continues to operation 258.

At operation 258, a cadence acquired output is generated. Various embodiments generate one or more cadence acquired outputs. Examples of cadence acquired outputs include generation of audible signals such as beeps, bells, sound effects, pre-recorded voiceovers (e.g., "Cadence detected: 180 steps per minute"), etc. Other example of cadence acquired outputs include visual indicators that the cadence was detected or of the detected cadence on the user interface 164.

Additionally, in some embodiments one or multiple media content items (e.g., a playlist) are selected for playback by the media-playback device 102 based on the acquired cadence. In some embodiments, the media content items include music with a tempo that corresponds to the acquired cadence. And the media content items that are played back can be stored locally in a file or streamed from an external source such as the media-delivery system 104. For example, in some embodiments, the media-playback device 102 requests media content items that correspond to the acquired cadence.

Some embodiments do not include a separate cadence acquired output. Instead, the media output that is played back serves as an indication to the user that the cadence has been acquired.

At operation 260, the cadence is monitored. In some embodiments, the cadence is monitored by continuing to detect the cadence associated with a repetitive movement of the media-playback device 102. In other embodiments, the cadence is monitored by continuing to acquire a cadence from a separate device, a user input, or otherwise.

At operation 262, it is determined whether the cadence has changed. In some embodiments, the cadence is determined to have changed when the acquired cadence is different than the current cadence (i.e., the cadence used for playback of media content items) by more than a predetermined threshold. Additionally, in some embodiments, the cadence is determined to change when the acquired cadence is different than the current cadence for at least a predetermined duration (e.g., measured in terms of time, number of steps or other movements, etc.). In some embodiments, the predetermined threshold and predetermined duration are selected to distinguish intentional changes in cadence from short-term, environment-based adjustments. Examples of environment-based adjustments include slowing down to cross a street or dodge a puddle, changing cadence to traverse a staircase, changing cadence to turn, etc. In some embodiments, the intentionality of a change in cadence is determined based on a combination of the magnitude of difference and the duration of the change (e.g., a larger magnitude of difference requires a shorter duration to indicate an intentional change in cadence than a smaller magnitude of difference would, or vice versa, etc.). Additionally, some embodiments of the media-playback device 102 include an altimeter and changes in cadence that occur while the altitude measurement is changing rapidly are ignored (e.g., to ignore changes in cadence that occur while traversing a staircase, etc.). In addition, in some embodiments, changes in cadence that occur while the media-playback device 102 is changing direction are ignored. Some embodiments include a compass to determine when the media-playback device 102 is changing directions. Additionally, the location-determining device 150 is used to determine when the media-playback device 102 is changing directions in some embodiments.

If it is determined that a change in cadence has occurred the method continues to operation 264 in which a cadence changed output is generated and media content is played back based on the changed cadence. Various embodiments generate one or more change in cadence outputs. Examples of change in cadence outputs include generation of audible signals such as beeps, bells, sound effects, pre-recorded voiceovers (e.g., "New cadence detected: 170 steps per minute"), etc. Other examples of change of cadence outputs include visual indicators that a change in cadence was detected or of the changed cadence on the user interface 164.

Additionally, in some embodiments one or multiple media content items (e.g., a playlist) are selected for playback by the media-playback device 102 based on the changed cadence. As discussed above with respect to operation 258, in some embodiments, the media content items include music with a tempo that corresponds to the changed cadence. And the media content item that is played back can be stored locally in a file or streamed from an external source such as the media-delivery system 104. For example, in some embodiments, the media-playback device 102 requests media content items that correspond to the changed cadence.

In some embodiments, the media content items selected for playback based on the changed cadence are immediately played back after the change in cadence is detected (with or without beat alignment and crossfading). In other embodiments, the media-playback device completes playback of the currently playing media content item before beginning to playback the newly selected media content items. Further, in some embodiments, the media-playback device 102 continues to playback the currently-playing media content item from a buffer until a second buffer can be sufficiently populated with stream data corresponding to the newly selected media content items.

Some embodiments do not include a separate change of cadence output. Instead, the change to the media content that is being played back operates as an indication to the user that a change in cadence has been detected.

After operation 264, the method 250 returns to operation 260 where the cadence is monitored. Similarly, if it is determined that a change in cadence has not occurred at operation 262, the method returns to operation 260, where the cadence continues to be monitored.

Figure 4:
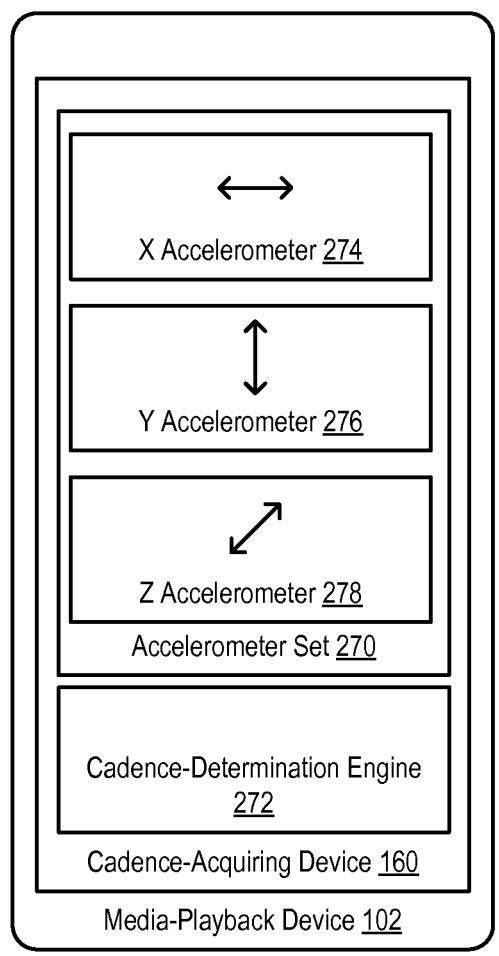
FIG. 4 illustrates an example cadence-acquiring device of FIG. 2.

FIG. 4 illustrates an example cadence-acquiring device 160. In the embodiment illustrated in FIG. 4, the cadence-acquiring device 160 operates to determine a cadence associated with a user based on movement of the media-playback device 102. In this example, the cadence-acquiring device 160 includes accelerometer set 270 and cadence-determination engine 272. Although the examples described herein use accelerometers, in other embodiments other types of movement-determining devices are used. A movement-determining device is a device that operates to capture measurements related to movement of the media-playback device. An accelerometer is an example of a movement-determining device.

The accelerometer set 270 includes at least one accelerometer. An accelerometer is a device that is used to measure acceleration, including gravitational acceleration. In some embodiments, an accelerometer measures acceleration in a single direction. In other embodiments, an accelerometer measures acceleration in more than one direction, such as in three directions. In some embodiments, the orientation of an accelerometer (and therefore the orientation of the media-playback device 102) is inferred by comparing the measured direction and magnitude of acceleration to an expected direction and magnitude of gravitational acceleration. Additionally, in some embodiments, the motion of the accelerometers is inferred from one or more measured acceleration values.

In the example shown, the accelerometer set 270 includes three accelerometers: an X accelerometer 274, a Y accelerometer 276, and a Z accelerometer 278. In this example, the X accelerometer 274 operates to measure acceleration in a horizontal direction relative to the media-playback device 102. Similarly, in this example, the Y accelerometer 276 operates to measure acceleration in a vertical direction relative to the media-playback device 102. Similarly, in this example, the Z accelerometer 278 operates to measure acceleration in a front-to-back direction relative to the media-playback device 102. In other embodiments, the accelerometer set 270 includes three accelerometers that each operate to measure acceleration in three orthogonal directions (i.e., each of the three directions is pairwise perpendicular to the other two directions). In this manner, the accelerometer set 270 operates to determine acceleration in three-dimensional space.

The cadence-determination engine 272 operates to determine a cadence based at least in part on the measurements from the accelerometer set 270. In some embodiments, the cadence-determination engine 272 analyzes sequences of measurements captured by one or more of the accelerometers. A series of measurements captured over intervals during a particular duration is an example of a sequence of measurements. An example method of determining cadence is illustrated and described with respect to at least FIG. 5.

However, as noted above, some embodiments of the cadence-acquiring device 160 do not include the accelerometer set 270 or the cadence-determination engine 272. In these embodiments, the cadence-acquiring device 160 may operate to receive a cadence value over a network from an external device or to receive a user input representing a cadence value.

Figure 5:
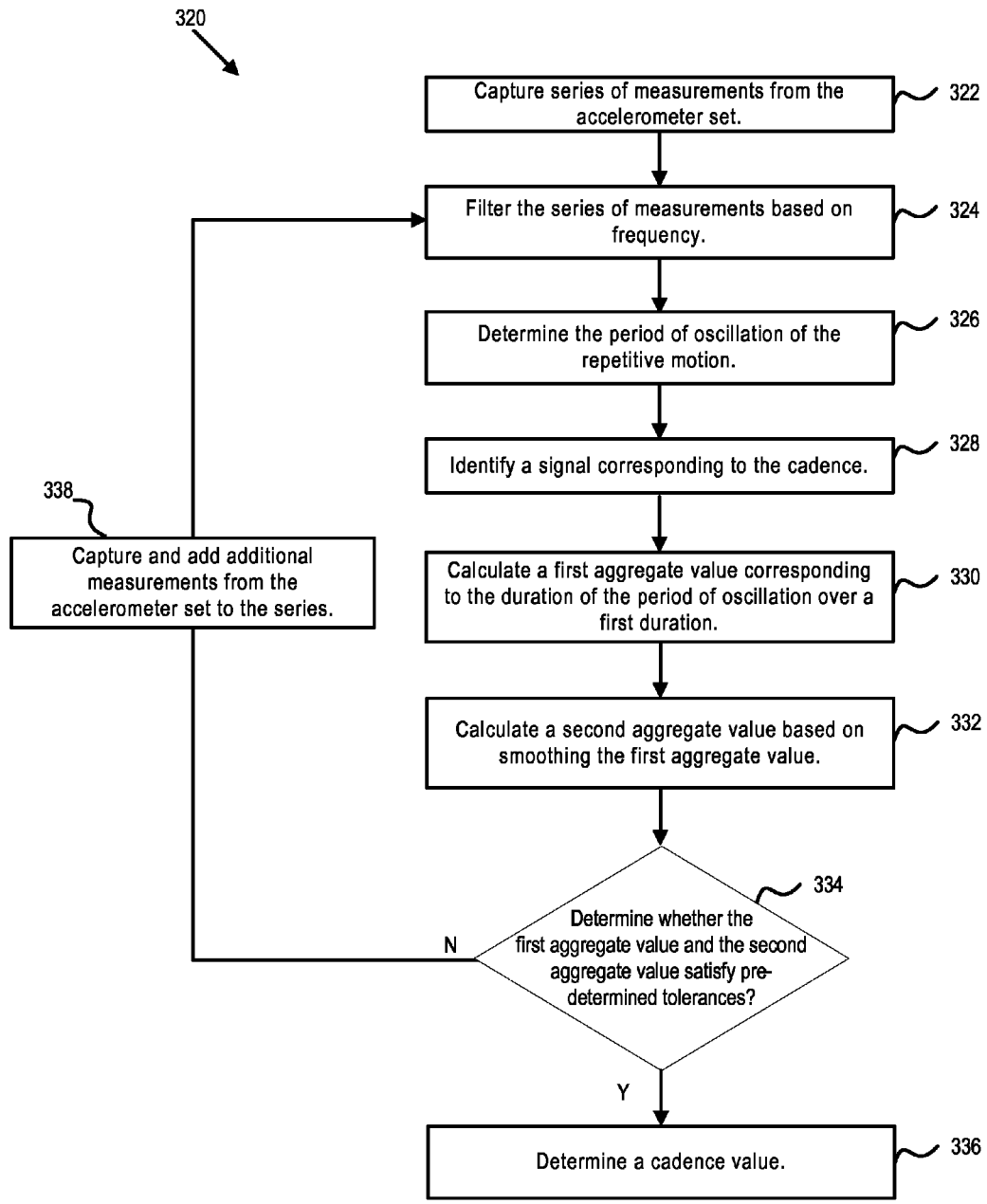
FIG. 5 illustrates an example method of determining cadence performed by some embodiments of the cadence-determination engine of FIG. 2.

FIG. 5 illustrates an example method 320 of determining cadence performed by some embodiments of the cadence-determination engine 272 using the accelerometer set 270.

At operation 322, a series of measurements is captured from one or more accelerometers of the accelerometer set 270. For purposes of this example, the method 320 will be described when measurements are captured from a set of three orthogonally-oriented accelerometers. However, other embodiments capture measurements from different numbers and different configurations of accelerometers.

In at least some embodiments, the measurements are captured at a sample rate of 50 Hz. In other embodiments, the measurements are captured at a different sample rate such as a sample rate in the range of 20-200 Hz. Generally, with higher sample rates there will be less error in calculating the cadence. Other embodiments may use different sample rates, including variable sample rates, as well. In at least some embodiments, the captured samples from each accelerometer are stored as a separate series of data points.

In some embodiments, the captured measurements are amplified. For example, the acceleration measurements may be quite small when a user places the media-playback device 102 on a treadmill rather than holding it. By amplifying the measurements, the media-playback device 102 operates to sense a cadence from smaller vibrations transmitted through the treadmill. In some embodiments, the captured measurements are amplified if none of the signals from any of the accelerometers exceed a pre-defined threshold for a specific period of time. Furthermore, some embodiments operate to amplify the captured measurements if the location-determining device 150 indicates that the user is indoors or stationary.

At operation 324, the series of measurements are filtered based on frequency to generate filtered signals. For example, in some embodiments, each of the series are filtered with a band-pass filter such as a band-pass filter comprising third-order Butterworth filters. Beneficially, Butterworth filters provide a generally flat frequency response and thus allows for reliable energy estimation of the filtered signal. Furthermore, a third-order Butterworth filter provides a steep enough response to discard/attenuate signals outside of the desired region. Other embodiments, however, use other types of band-pass filters. For example, some embodiments use a fifth-order Butterworth filter. In some embodiments, the band-pass filter is tuned to pass the portion of the signal in the series that is likely to correspond to running (e.g., having a frequency of 140-200 steps per minute). For example, the band-pass filter may discard frequencies below 140 steps per minutes (e.g., walking, holding the media-playback device 102, etc.) and above 200 steps per minute (e.g., vibrations).

Figure 6:
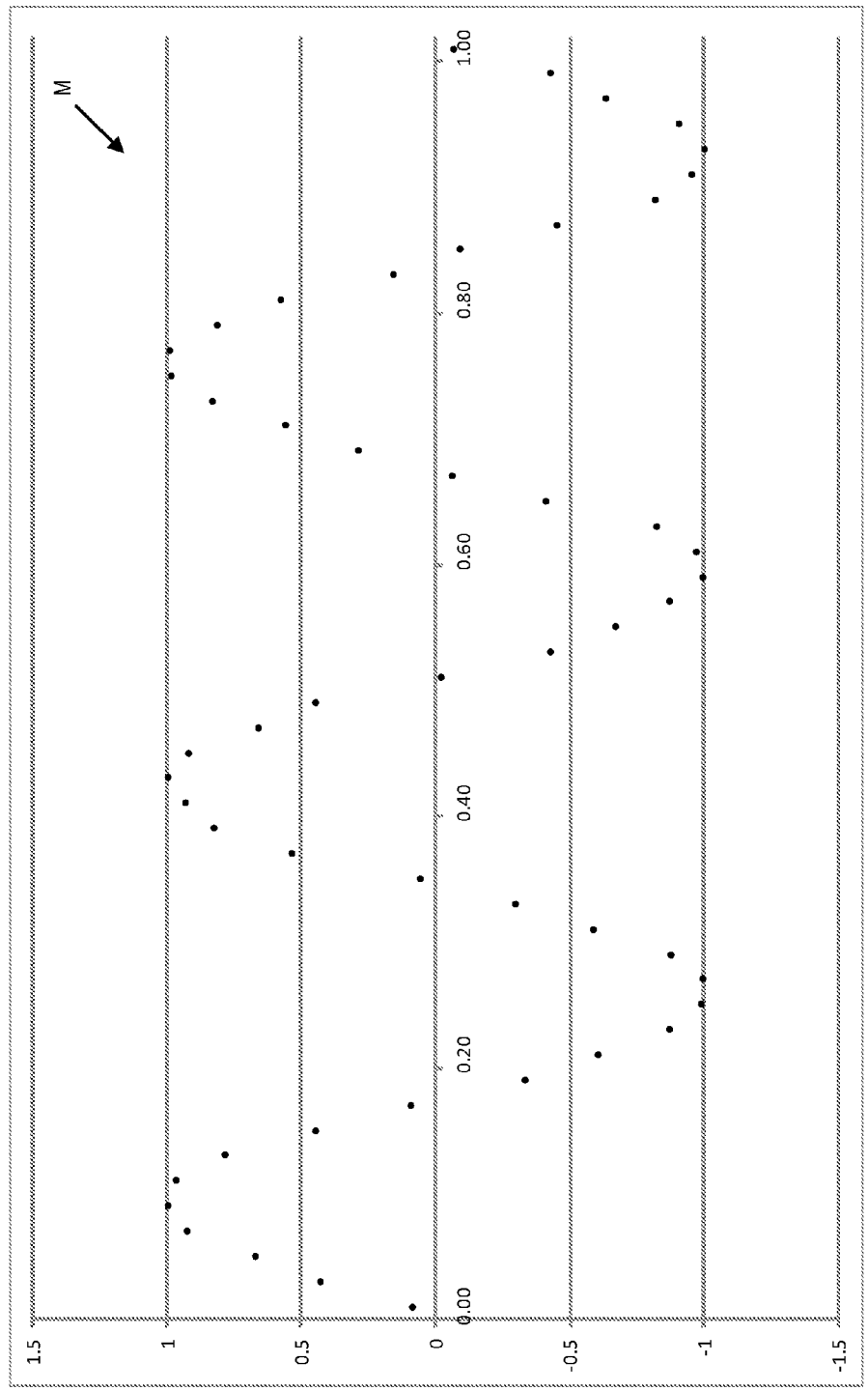
FIG. 6 shows an example series of filtered sample measurements from the accelerometer of FIG. 4.
Figure 7:
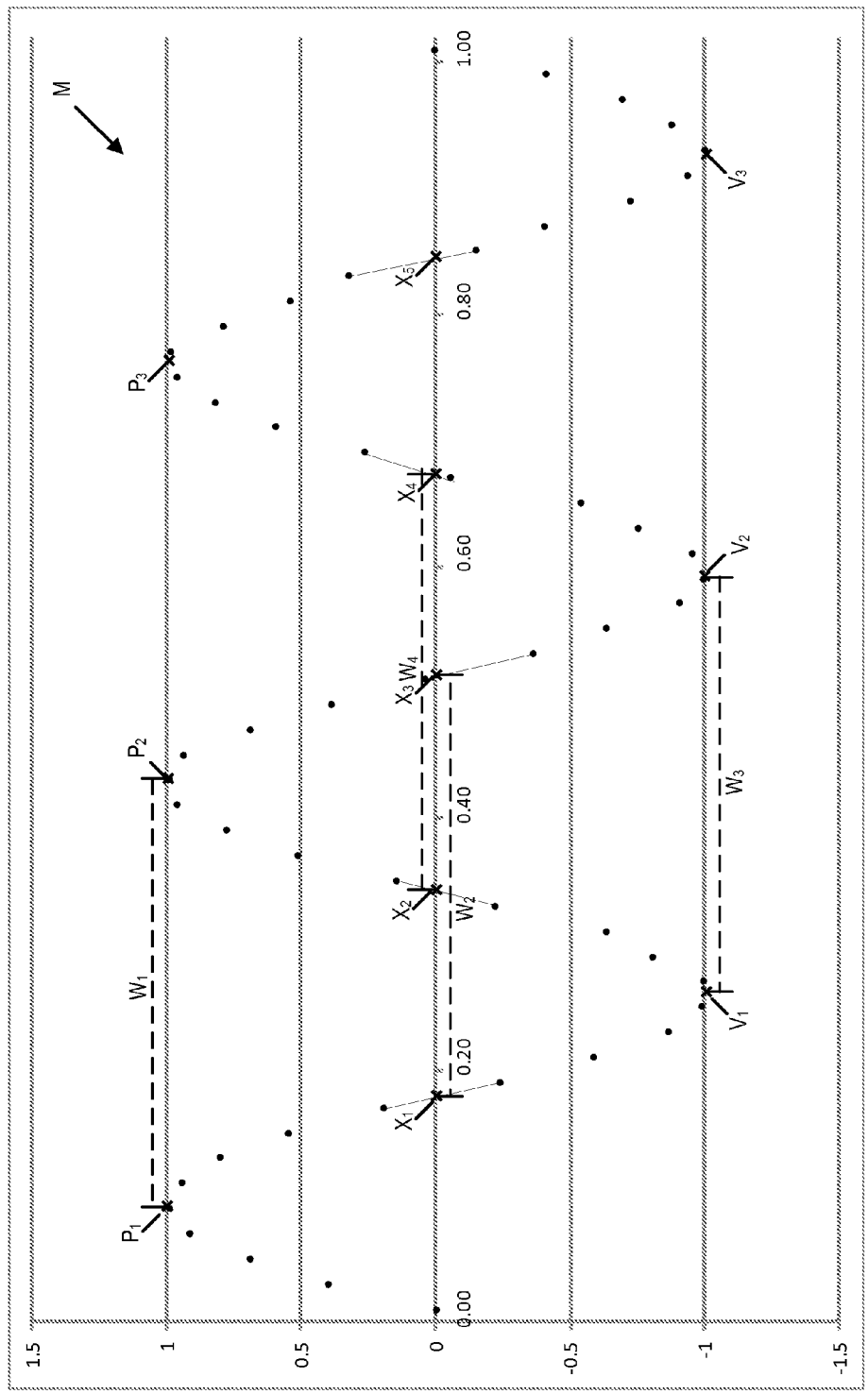
FIG. 7 shows the example series of filtered sample measurements of FIG. 6 with additional annotations to identify portions of the signal that are used in analyzing the periodicity of the repetitive motion.

At operation 326, the filtered signals are analyzed to determine the period of oscillation of the repetitive motion. FIGS. 6 and 7, which are discussed below, illustrate samples from an example signal and corresponding periods of repetitive motion. FIG. 6 shows an example series of filtered sample measurements M from an accelerometer captured over one second. FIG. 7 shows the same series of filtered sample measurements M with additional annotations to identify portions of the signal that are used in analyzing the periodicity of the repetitive motion. In some embodiments, each of the signals captured (i.e., the samples from each of the accelerometers in the accelerometer set) are analyzed to determine the period of oscillation of the repetitive motion. In other embodiments, a single signal is determined to be indicative of the cadence (see operation 328), and only this single signal is analyzed to determine the period of oscillation for the repetitive motion of that signal (operation 326). Therefore in some embodiments the operation 328 may be performed before operation 326.

In some embodiments, the period of repetitive motion is estimated by analyzing the filtered signals to identify (or approximate) zero crossings of the signal. In some embodiments, the zero crossings of the signal are approximated by linearly interpolating between two adjacent samples that are on opposite sides of zero. In FIG. 7, five example approximated zero crossings are shown as zero crossings $X_1$-$X_5$. Additionally, in some embodiments, minima and maxima are also identified (or approximated) for each oscillation. In some embodiments, a parabolic approximation is used to approximate the minima and maxima of each oscillation. Other embodiments may use the value of a local minimum or maximum sample point. In FIG. 7, the maxima (peaks) are shown as maxima $P_1$-$P_3$ and the minima (valleys) are shown as minima $V_1$-$V_3$.

In some embodiments, the period of the repetitive motion is then estimated by measuring the distance between equivalent points in adjacent oscillations. For example, in some embodiments, the period is estimated by calculating the distance between adjacent wave maxima (e.g., in FIG. 7, width $W_1$ between the maxima $P_1$ and the maxima $P_2$). Similarly, the period can be estimated by calculating the distance between adjacent falling zero crossings (e.g., in FIG. 7, width $W_2$ between the zero crossing $X_1$ and the zero crossing $X_3$) and between adjacent rising zero crossings (e.g., in FIG. 7, width $W_4$ between the zero crossing $X_2$ and the zero crossing $X_4$). Additionally, the period can be estimated by calculating the distance between adjacent wave minima (e.g., in FIG. 7, the width $W_3$ between minima $V_1$ and minima $V_2$). In this manner, the width of a period of a single oscillation is measured four times, with the measurements being offset from each other by quarter oscillations.

In some embodiments, during operation 326, a single measurement of the period of oscillation for each of the signals (e.g., from each of the accelerometers) is calculated and stored. In some embodiments, this single measurement is added to a First-In-First-Out buffer that operates as a circular buffer for storing a predetermined number of measurements. As operation 326 is repeated, the FIFO buffer fills up with measurements. When the FIFO buffer is full, new measurements replace the oldest measurement in the FIFO buffer. In this manner, the FIFO buffer operates to store a predetermined number of the most recent measurements of the period of oscillation. Some embodiments include multiple FIFO buffers and each of the multiple FIFO buffers is configured to store measurements determined from a different accelerometer. However, as noted above, in some embodiments, measurements are only determined for a single signal. In these embodiments, a single FIFO buffer may be used to store the measurements from the signal that has been identified as corresponding to cadence.

In at least some embodiments, one or more FIFO buffers are configured to each store twenty-four measurements. Because these width measurements are calculated at every quarter step, twenty-four measurements are captured across approximately six steps (which takes two seconds at an example running cadence of 180 steps per minute). Because the FIFO queues are updated based upon oscillations occurring in the filtered signals in some embodiments, if the user stops running and stands still, the FIFO buffer will not be updated (and beneficially the calculated cadence will not be impacted by the stop).

In some embodiments, the measurements stored in the FIFO buffer or buffers are converted to a log base 2 scale. Beneficially, when the measurements are converted to a log base 2 scale, the measurements remain linear across a range of cadence values.

At operation 328, a signal corresponding to the cadence is identified. In some embodiments, the signal corresponding to the cadence is a signal from at least one of the accelerometers that is most likely correlated with cadence. Because the orientation of the media-playback device 102 relative to the user U may not be fixed (e.g., when the media-playback device 102 is a smartphone or other mobile device), some embodiments analyze the signals captured by the various accelerometers to determine which of the accelerometers is oriented to detect movement in the direction of the repetitive motion at a given time. In other embodiments, a signal corresponding to the direction of relevant movement may be identified by combining the signals captured by multiple of the accelerometers.

In some embodiments, the signal corresponding to the direction of relevant movement is identified based on identifying the filtered accelerometer signal having the highest energy. In some embodiments, the energy of each of the filtered signals is calculated by rectifying the filtered signal and convoluting the rectified signal with a Hanning window of fifty samples (i.e., one second worth of samples at fifty Hz). Other embodiments use a number of samples selected from the range 10-100 samples. In some embodiments, other techniques are used to calculate the energy of the filtered signals.

In some embodiments, the highest energy signal is determined after each sample is recorded. In other embodiments, the highest energy signal is determined at a different interval. Further, in at least some embodiments, the identity of the highest energy signal is tracked (e.g., after every sample or every tenth sample) so that the identity of the highest-energy signal (and therefore the direction of the repetitive movement) can be updated if necessary. Beneficially, by tracking the highest energy signal, changes in the orientation of the media-playback device 102 will not interfere with identifying the accelerometer associated with the direction of the repetitive movement. In some embodiments, a signal corresponding to the cadence is identified by combining portions of multiple filtered series from different accelerometers to include the data from the series having the highest energy over each time interval.

In other embodiments, other methods of determining the direction of relative movement are used. For example, if the orientation of the media-playback device 102 relative to the user U is known or can be inferred, the signal from a particular accelerometer may be identified as corresponding to the expected direction of relevant motion based on the direction of movement to which the particular accelerometer is sensitive (which can be inferred from the orientation of the media-playback device 102 relative to the user). As an example, if the media-playback device 102 is oriented in an upright position, it can be inferred that that the Y-accelerometer 276 will be sensitive to vertical movement such as would be expected from running. In this example, the signal from the Y-accelerometer 276 is used in some embodiments.

At operation 330, a first aggregate value corresponding to the period of the oscillation over a first duration is calculated. In some embodiments, the first duration is based on a predetermined number of oscillations, such as six oscillations. Other embodiments have a first duration based on a different predetermined number of oscillations such as 4-10 oscillations. In other embodiments, the first duration corresponds to a predetermined time period such as 2-10 seconds.

In some embodiments, the first aggregate value is calculated by averaging multiple estimated widths of the period of oscillation. For example, in some embodiments, twenty-four estimated width values captured every quarter oscillation (e.g., the values stored in the FIFO buffer described at least with respect to operation 326) are averaged to generate the first aggregate value. In some embodiment, the FIFO buffer is updated with a new value every quarter oscillation and the first aggregate value is also recalculated every quarter oscillation using the updated values in the FIFO buffer. In some embodiments, the FIFO buffer is pre-populated with measurements that correspond to a typical cadence at the start of method 320 so that a reasonable first aggregate value may be calculated before enough measurements have been captured to fully fill the FIFO buffer. In some embodiments, the typical cadence value used to generate values to prepopulate the FIFO buffer is 165 steps per minute. In other embodiments, the typical cadence is calculated based on historic cadence information associated with the user (such as cadence data captured from previous similar activities performed by the user). Because the first aggregate value is based on averaging multiple measurements, in at least some embodiments, the aggregate value is not significantly affected by intermittent sampling errors or minor, short variations in cadence.

Furthermore, in some embodiments, a series of first aggregate values is generated as additional measurements are captured. In some embodiments, each of the values in the series of first aggregate values correspond to the period of oscillation at different time intervals over which the series of measurements span. In some embodiments, a first aggregate value is generated and included in the series after every quarter oscillation. In other embodiments, the first aggregate value is generated at a different frequency such as once every oscillation, once every second oscillation, etc.

At operation 332, a second aggregate value is calculated based on smoothing the first aggregate value. In some embodiments, the second aggregate value is updated (or re-calculated) when the first aggregate value is updated. In some embodiments, the second aggregate value is calculated using equation 1 shown below:

$$y(i)=y(i-1)+\alpha \times (x(i)-y(i-1)) \quad (1)$$

where
- $y(i)$ represents the currently calculated value for the second aggregate value;
- $y(i-1)$ represents the previously calculated value for the second aggregate value;
- $x(i)$ represents the most recently calculated value for the first aggregate value (e.g., as calculated by operation 330); and
- $\alpha$ is a smoothing coefficient.

In some embodiments, the smoothing coefficient $\alpha$ is 0.07. In other embodiments, the smoothing coefficient $\alpha$ is a value selected from the range 0.01-0.25. In yet other embodiments, the smoothing coefficient $\alpha$ is a value selected from the range 0.01-0.99. The smoothing coefficient $\alpha$ is related to the sample rate; accordingly, in some embodiments with higher sample rates, lower values are used for the smoothing coefficient $\alpha$. The smoothing coefficient $\alpha$ causes the second aggregate value to change more slowly than the first aggregate value changes in response to changes in cadence. In some embodiments, the second aggregate value is initially set to a value that corresponds to a cadence that is slightly lower than would be expected for the activity. For example, in some embodiments that relate to running, the second aggregate value is initially set to a value corresponding to a cadence of 140 steps per minute. In other embodiments, the second aggregate value is initially set to a value that is twenty-five steps per minute less than the user's historic average cadence for the activity.

In at least some embodiments, other equations or techniques are used to smooth the second aggregate value. Embodiments are possible using any technique for smoothing the second aggregate value in which a previously computed value for the second aggregate value is used in computing an updated value for the second aggregate value.

Like the first aggregate value, in some embodiments, a series of second aggregate values is generated as additional measurements are captured. In some embodiments, each of the values in the series of second aggregate values correspond to a smoothed first aggregate value for different time intervals over which the series of measurements span. Also like the series of first aggregate values, in various embodiments, the values in the series of second aggregate values are generated at various frequencies such as after every quarter oscillation, after every oscillation, after every other oscillation, etc.

At operation 334, it is determined whether the first aggregate value and the second aggregate value satisfy predetermined tolerances. As noted above, the second aggregate value changes more slowly than the first aggregate value changes in response to a change in cadence (e.g., when the user first starts running, when the runner changes cadence, etc.). Accordingly, in some embodiments, the difference between the first aggregate value and the second aggregate value indicates whether the user's cadence has been stable or changing recently.

In some embodiments, the predetermined tolerances include both a difference tolerance and a duration requirement. An example of a difference tolerance is predetermined number of steps per minute difference between the first aggregate value and the second aggregate value (e.g., within two steps per minute, or within a certain duration of time measured on a linear or log base 2 scale, etc.). An example of a duration requirement is a requirement that the first aggregate value and the second aggregate value satisfy the difference tolerance for a predetermined duration (e.g., the first aggregate value is within two steps per minute of the second aggregate value for at least two steps). In some embodiments, the predetermined duration is measured in steps, time, or otherwise.

If it is determined that the first aggregate value and the second aggregate value satisfy predetermined thresholds, the method 320 continues to operation 336 where the cadence is determined. If not, the method 320 continues to operation 338 where additional measurements are captured from the accelerometers in the accelerometer set and the process repeats starting at operation 324.

At operation 336, a cadence value is determined. In some embodiments, the cadence value is determined based on the second aggregate value. To determine a cadence value from the second aggregate value, the second aggregate value may need to be converted from a duration in log base 2 scale to a frequency value. Once the cadence value has been determined, it can be used for many purposes, including selecting appropriate media content items.

In some embodiments, the method 320 is used to both determine an initial cadence and to detect changes in cadence throughout an activity. As noted above, to detect an initial cadence, the FIFO buffer or buffers and second aggregate values may be set to certain initial values that are selected to minimize the number of steps (or time) required to accurately detect a stable cadence. For example, by populating the FIFO buffer or buffers with values that correspond to an expected (or typical) cadence value, the first aggregate value calculated by operation 330 will immediately be close to a value that corresponds to the user's instantaneous cadence. As another example, initially setting the second aggregate value to a value that corresponds to a cadence that is slightly outside of the expected range may prevent falsely determining a stable cadence before the user has actually reached a stable cadence. Instead, a stable cadence will be determined after the user has performed with a stable cadence for a sufficient time to cause the initially low second aggregate value to converge towards the first aggregate value. In some embodiments, a stable cadence is detected within ten to fifteen steps.

In some embodiments, a third aggregate value is calculated in a manner similar to the calculation of the second aggregate value (as described above with respect to operation 332). The third aggregate value may be used to determine when the user has changed cadence after an initial cadence has been determined. In some embodiments, the third aggregate value represents a smoothing of the second aggregate value. In this manner, the third aggregate value trails the second aggregate value and takes a longer time to react to changes in cadence. Additionally, in some embodiments, when the third aggregate value and the second aggregate value are within a predetermined difference threshold of each other for a predetermined duration threshold it is determined that the detected cadence value has stabilized. If the detected cadence value has stabilized at a value that is different from the previously determined cadence by a sufficient threshold a new cadence value is determined (and may be used in media content selection or otherwise). Examples of sufficient thresholds include two steps per minute, five steps per minute, or ten steps per minute. In some embodiments, the sufficient threshold is a value selected from the range 1-15 steps per minute.

In at least some embodiments, the third aggregate value is calculated using an equation that is similar to equation 1 (described above with respect to operation 332) such as equation 2 shown below:

$$z(i)=z(i-1)+\beta \times (y(i)-z(i-1)) \quad (2)$$

where
- $z(i)$ represents the currently calculated value for the third aggregate value;
- $z(i-1)$ represents the previously calculated value for the third aggregate value;
- $y(i)$ represents the most recently calculated value for the second aggregate value (e.g., as calculated by operation 332); and
- $\beta$ is a second smoothing coefficient.

In some embodiments, the second smoothing coefficient $\beta$ is 0.02. In other embodiments, the second smoothing coefficient $\beta$ is a value selected from the range 0.001-0.1. In yet other embodiments, the smoothing coefficient $\alpha$ is a value selected from the range 0.001-0.99. Like the smoothing coefficient $\alpha$, the smoothing coefficient $\beta$ is related to the sample rate; accordingly, in some embodiments with higher sample rates, lower values are used for the smoothing coefficient $\beta$. The second smoothing coefficient $\beta$ causes the third aggregate value to change even more slowly than the second aggregate value changes in response to changes in cadence. As mentioned above with respect to the second aggregate value, the third aggregate value is also calculated using other smoothing equations in some embodiments.

Like the first aggregate value and the second aggregate value, in some embodiments, a series of third aggregate values is generated. The values in the series of third aggregate values correspond to smoothed second aggregate values over various intervals over which the series of measurements span. The values in the series of third aggregate values may be generated at the same frequency as the values in the series of second aggregate values or at a different frequency.

Figure 8:
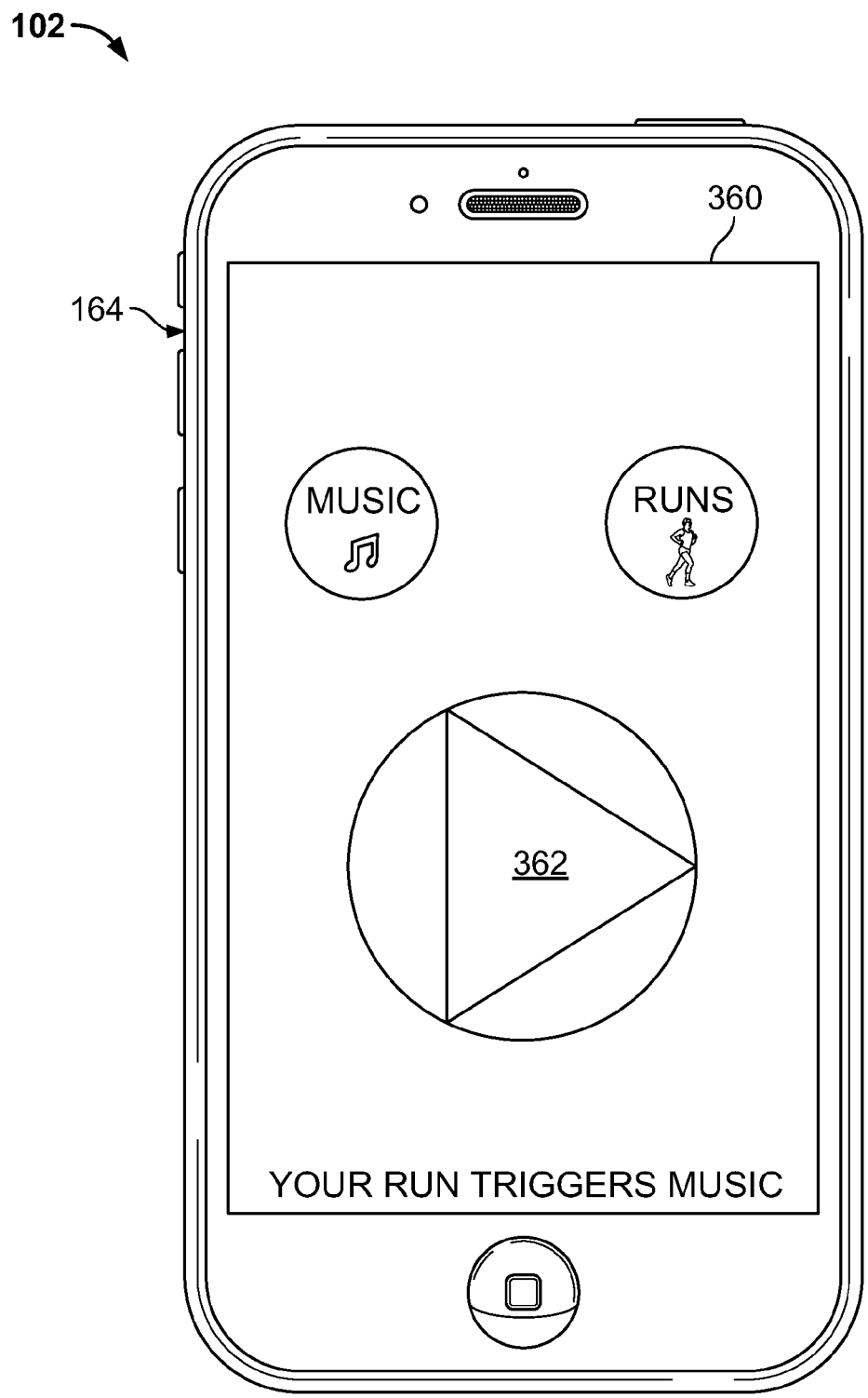
FIG. 8 shows an example start screen displayed by some embodiments of the user interface of FIG. 2.

Referring now to FIG. 8, an example start screen 360 displayed by some embodiments of the user interface 164 of the media-playback device 102 is shown. In some embodiments, the start screen 360 is displayed when the media-playback device 102 is first activated, when a particular application (or "app") (e.g., the media-playback engine 166) is launched on the media-playback device 102, or upon receiving a particular command (e.g., a menu selection to start the cadence-based media content selection engine 168) within an application. The example start screen 360 includes a start control 362. The start control 362 operates to receive a user input to indicate that the user is ready to begin running and desires for the media-playback device 102 to perform one or more of cadence acquisition and cadence-based media selection. In some embodiments, the start control 362 operates to receive a touch input from a selector. In other embodiments, the start control 362 operates to receive user input by other means (e.g., a mouse click, etc.).

Figure 9:
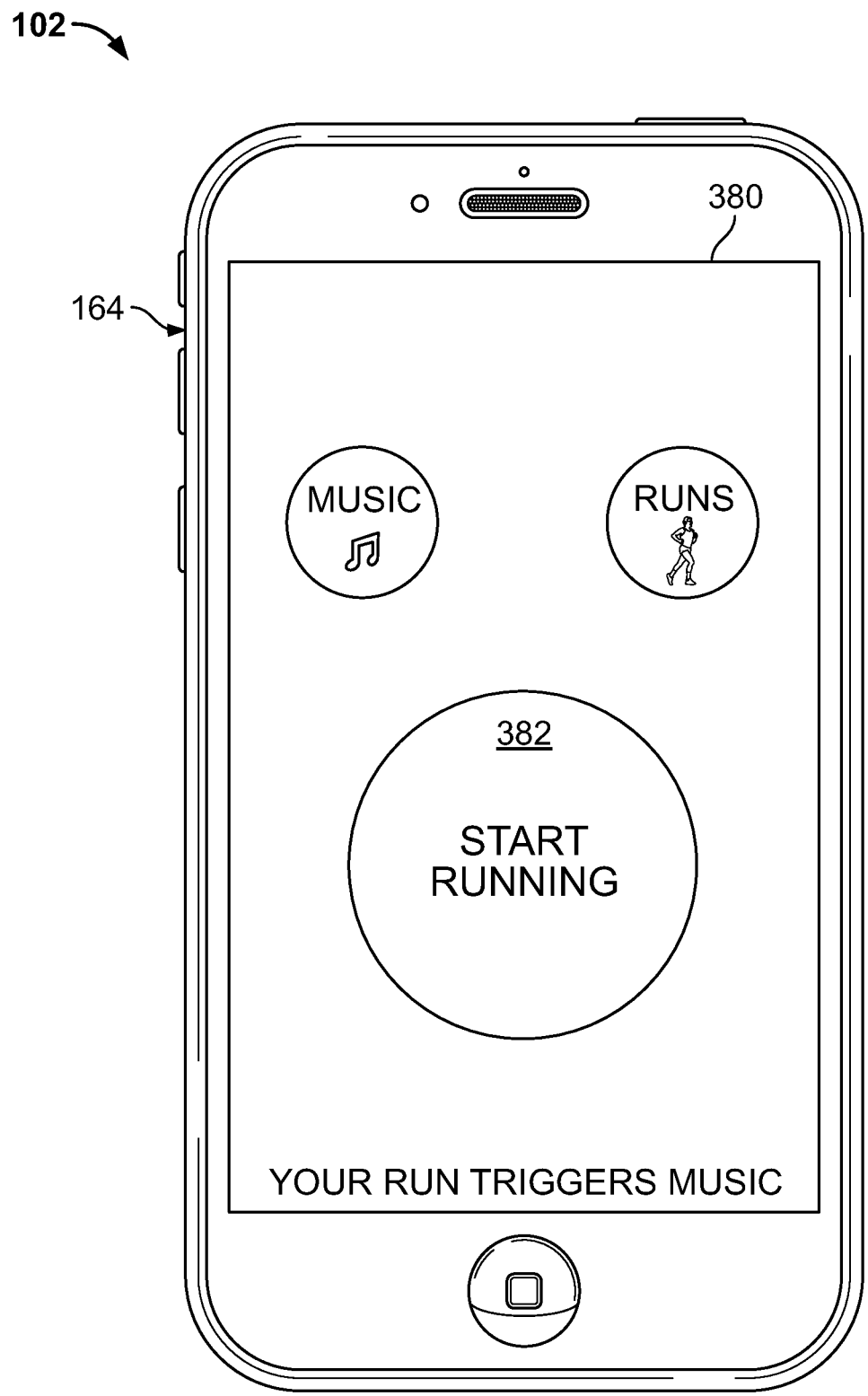
FIG. 9 shows an example start activity screen displayed by some embodiments of the user interface of FIG. 2.

Referring now to FIG. 9, an example start activity screen 380 displayed by some embodiments of the user interface 164 of the media-playback device 102 is shown. In some embodiments, the start activity screen 380 is displayed in response to actuation of the start control 362 and operates to communicate to a user that the media-playback device 102 is ready to perform cadence acquisition. The example start activity screen 380 includes a start activity instruction message 382. In the example shown in FIG. 9, the start activity instruction message 382 includes text that says "START RUNNING." Other embodiments are possible that show other instruction messages. Further, some embodiments of the start activity instruction message 382 include icons, images, video clips, etc. to communicate various information or instructions to the user. In some embodiments, the cadence-acquiring device 160 continuously attempts to acquire a cadence while the start activity screen 380 is being displayed.

Figure 10:
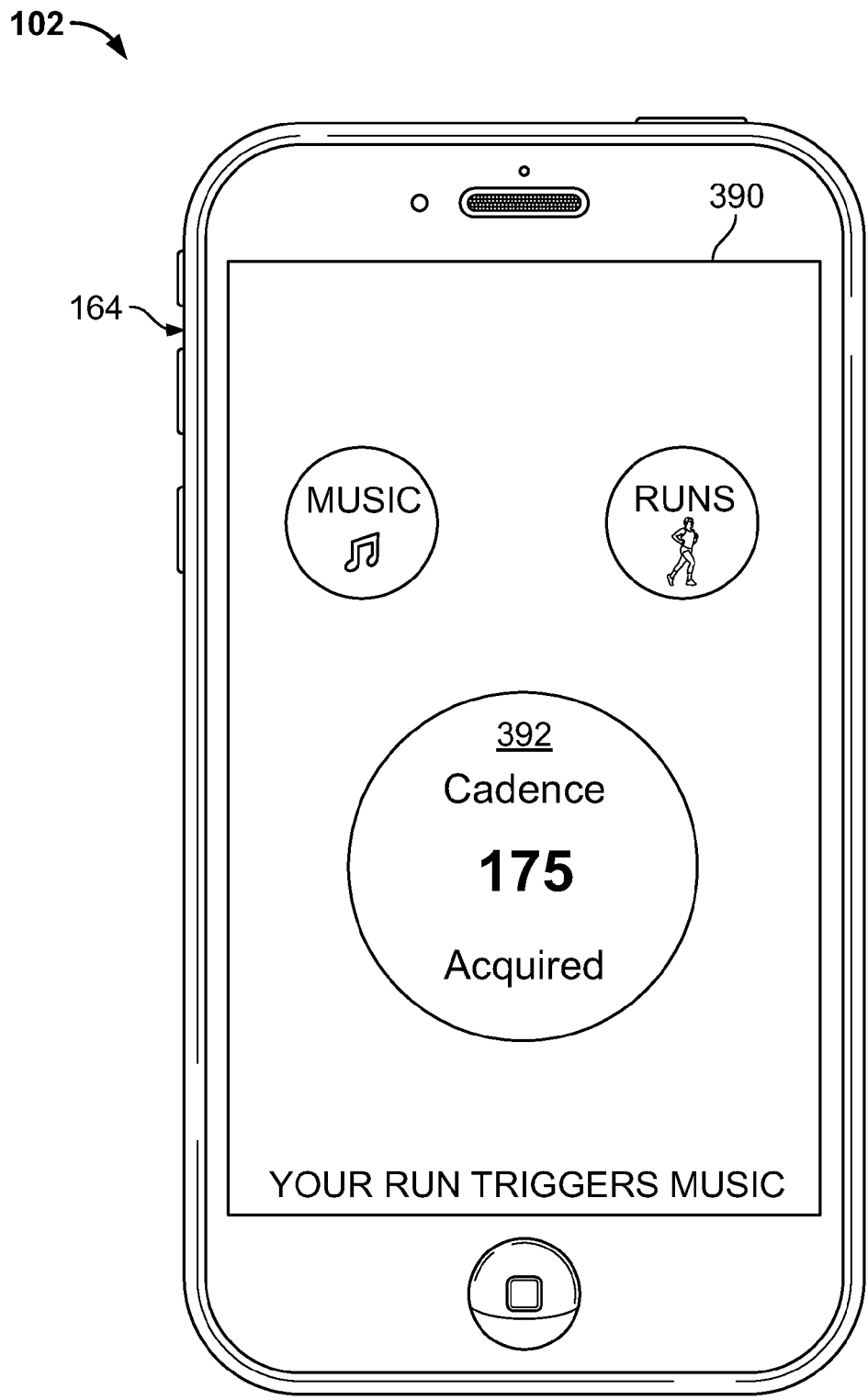
FIG. 10 shows an example cadence acquired screen displayed by some embodiments of the user interface of FIG. 2.

Referring now to FIG. 10, an example cadence acquired screen 390 displayed by some embodiments of the user interface 164 of the media-playback device 102 is shown. In some embodiments, the cadence acquired screen 390 is displayed in response after the media-playback device 102 has successfully performed an initial cadence acquisition. The example cadence acquired screen 390 includes a cadence acquired message 392. In some embodiments, the cadence acquired message 392 includes text to indicate that a cadence value has been acquired (e.g., "CADENCE ACQUIRED"). Additionally, in some embodiments, the cadence acquired message 392 includes text to indicate the cadence value that was acquired (e.g., 175 steps per minute in the example shown in FIG. 10). In some embodiments, the cadence acquired screen 390 is displayed only briefly or not at all. For example, a cadence-based content playback screen (such as the example illustrated and described with respect to at least FIG. 11) is shown instead of the cadence acquired screen 390 or shortly after the cadence acquired screen 390 is displayed.

Figure 11:
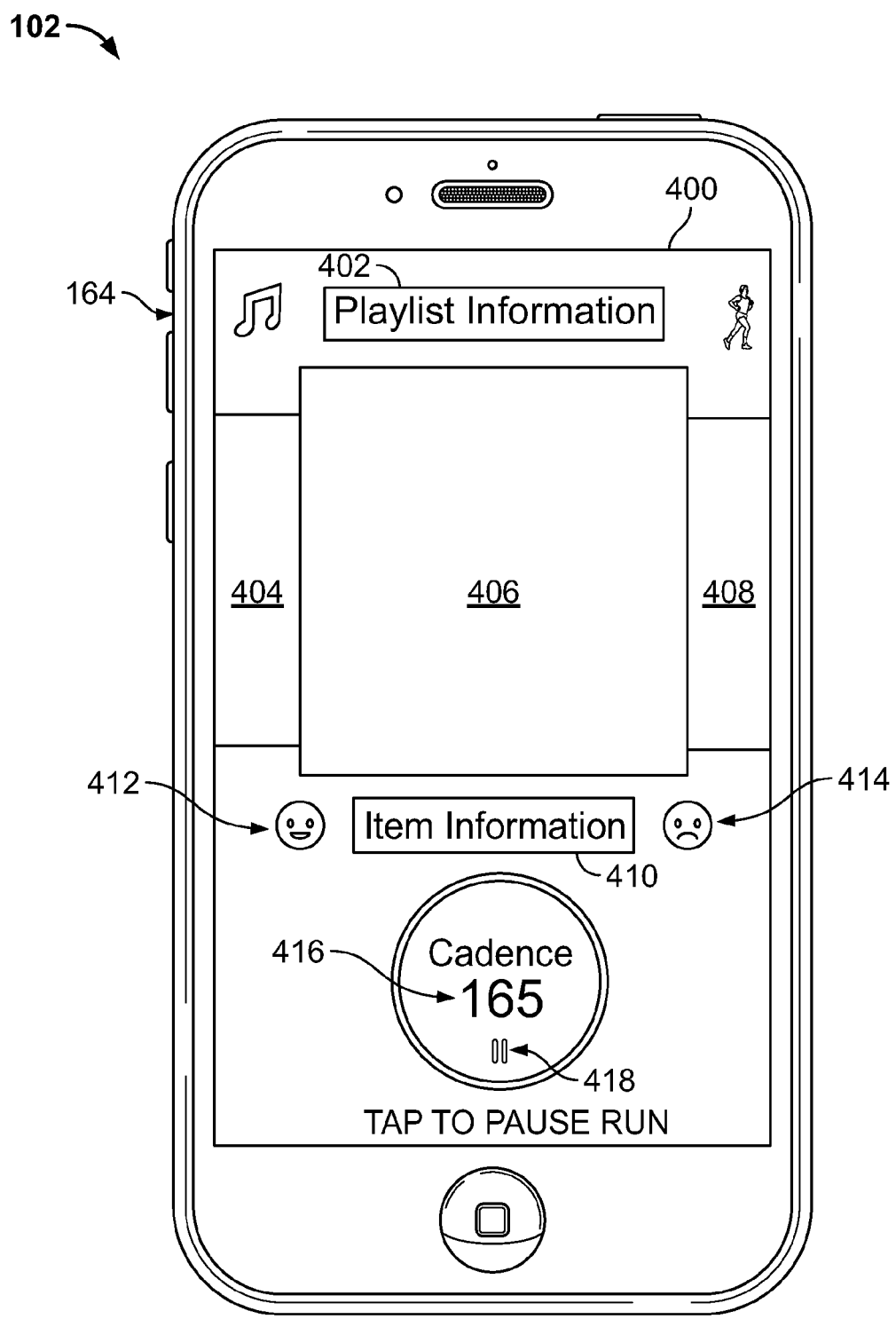
FIG. 11 shows an example cadence-based content playback screen displayed by some embodiments of the user interface of FIG. 2.

Referring now to FIG. 11, an example cadence-based content playback screen 400 displayed by some embodiments of the user interface 164 of the media-playback device 102 is shown. In some embodiments, the cadence-based content playback screen 400 is displayed in response to acquiring a cadence associated with a user activity. In some embodiments, the cadence-based content playback screen 400 includes a playlist information message 402, a previous media content item display panel 404, a current media content item display panel 406, a next media content item display panel 408, a current media content item information message 410, a dislike control 412, a like control 414, a cadence information message 416, and a pause control 418.

The playlist information message 402 operates to display information about the currently playing playlist of media content items. The playlist may be a pre-defined playlist of media content items that correspond to an acquired cadence or an ad-hoc playlist generated by the media-playback device 102 or the media-delivery system 104 based on the acquired cadence. In some embodiments, the playlist information message 402 displays a title provided with a pre-defined playlist (e.g. "Outdoor Running," "Spin Class," "Peak Performance," etc.). In some embodiments, the playlist information message 402 displays information that relates to the media content items included in an ad-hoc playlist such as a region (e.g., Sweden, Europe, U.S., etc.), a genre (e.g., Country, Rock, Rap, etc.), a mood (e.g., calm, happy, etc.), an era (e.g., 70's, 80's, 90's, 00's, etc.), or popularity (e.g., Top 50, etc.).

The previous media content item display panel 404 operates to display information about the previously played media content item such as an image associated with the previously played media content item (e.g., an album cover, an artist photograph, etc.). The current media content item display panel 406 and the next media content item display panel 408 operate similarly with respect to the currently playing media content item and the media content item that is schedule to play next. In some embodiments, the user interface 164 operates to cause the next or previous media content item to begin playback in response to detecting a swipe input to the left or right over the current media content item display panel 406. Additionally, in some embodiments, the user interface 164 operates to cause the previously played media content item to begin playback in response to detecting a touch input on the previous media content item display panel 404. Similarly, in some embodiments, the user interface 164 operates to cause the next media content item to begin playback in response to detecting a touch input on the next media content item display panel 408.

The current media content item information message 410 operates to display information about the currently playing media content item. Some embodiments display one or more of the following: a title, an artist name, an album name, a current position, a total length, and a tempo.

The dislike control 412 and the like control 414 operate to receive inputs indicating that a user dislikes or likes the currently playing media content item. In some embodiments, the media-playback device stores a like/dislike value associated with the currently playing media content item upon actuation of either the dislike control 412 or the like control 414. The value may be stored locally on the media-playback device 102 or remotely on the media-delivery system 104 or elsewhere. In some embodiments, one or both of the media-playback device 102 and the media-delivery system 104 use the like/dislike values that have been previously stored in selecting media content items for future playback. Additionally, in at least some embodiments, upon actuation of the dislike control 412, the currently playing media content item stops playing immediately or after a period of time and a new media content item begins to play.

The cadence information message 416 operates to present information to the user about the acquired cadence. In some embodiments, the cadence information message 416 displays a numeric value representing the acquired cadence. Additionally, in some embodiments, the cadence information message 416 also presents information related to whether the acquired cadence has recently changed. For example, the cadence information message 416 may include an arrow pointing up if the acquired cadence has recently increased and an arrow pointing down if the acquired cadence has recently decreased. Alternatively, the cadence may be displayed in a first color to indicate a recent increase, a second color to indicate a recent decrease, and a third color to indicate a stable cadence. As yet another alternative, the cadence information message 416 may blink or otherwise indicate the occurrence of a recent change in cadence. In yet another embodiment, the cadence information message 416 may operate to indicate how a currently acquired cadence compares to a goal or target cadence using any of the previously mentioned visual indicators. Additionally, in some embodiments, the cadence information message 416 operates to indicate if the media-playback device 102 has been unable to acquire a cadence valued (e.g., an error has occurred, the user is no longer running, etc.).

The pause control 418 operates to receive a pause input from the user. In some embodiments, the pause input triggers the media-playback device 102 to pause cadence acquisition. Beneficially, by pausing cadence acquisition, the user can take a break or otherwise change cadence without causing the playback of media content items to change. Users may take break for many reasons, such as to rest/recover, to wait to safely cross an intersection, or to wait for a running partner. Users may temporarily change cadence for many reasons as well such as to climb a stair case or a big hill, to cross rugged terrain, to weave through heavy traffic, etc. Additionally, in some embodiments, the pause input also triggers the media-playback device 102 to pause playback of the media content items.

As noted previously, although many of the examples provided above are described with respect to running, other embodiments relate to other repetitive motion activities as well such as cycling, swimming, and rowing.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A media-playback device comprising:
   a media-output device that plays media content items;
   a cadence-acquiring device comprising an accelerometer and a cadence-determination engine configured to:
   capture a sequence of measurements from the accelerometer;

filter the sequence of measurements based on frequency to generate a filtered sequence;
calculate a first aggregate value corresponding to a period of oscillation of the filtered sequence over a duration;
calculate a second aggregate value corresponding to a smoothing of the first aggregate value;
determine whether the first aggregate value and the second aggregate value satisfy predetermined tolerances, wherein the predetermined tolerances include a difference tolerance and a duration requirement; and
upon determining that the predetermined tolerances are satisfied, calculate a cadence value based on the first aggregate value; and
a cadence-based media content selection engine configured to:
identify a media content item based on the cadence determined by the cadence-determining engine; and
cause the media-output device to playback the identified media content item.

2. The media-playback device of claim 1, wherein the media-playback device is a smartphone.

3. The media-playback device of claim 1, wherein the cadence-based media content selection engine is further configured to upon the cadence-acquiring device acquiring a cadence, generate a cadence acquired output comprising at least one of an audible signal and a visual indicator.

4. The media-playback device of claim 1, wherein the cadence-based media content selection engine is configured to identify a media content item that includes music with a tempo that is within a predetermined threshold of the cadence.

5. The media-playback device of claim 1, wherein the cadence-based media content selection engine is further configured to:
monitor for changes in cadence determined by the cadence determining engine; and
upon detecting a change in cadence:
identify a second media content item based on a changed cadence; and
cause the media-output device to playback the identified second media content item.

6. The media-playback device of claim 5, wherein the cadence-based media content selection engine is further configured to, upon detecting a change in cadence, generate a cadence changed output.

7. The media-playback device of claim 1, wherein the duration is measured in terms of steps.

8. The media-playback device of claim 1, wherein the duration is measured in terms of time.

9. The media-playback device of claim 1, wherein the cadence-acquiring device comprises three orthogonally-oriented accelerometers and the cadence-determination engine is configured to:
capture sequences of measurements from each of the three accelerometers;
filter the sequences of measurements based on frequency to generate filtered sequences; and
identify the sequence of measurements corresponding to cadence, wherein the sequence is identified based on calculating an energy of each of the sequences.

10. The media-playback device of claim 1, wherein measurements are captured at a sample rate in the range of 20-200 Hz.

11. The media-playback device of claim 1, wherein the media content item is stored locally on the media-playback device.

12. The media-playback device of claim 1, wherein the media content item is streamed to the media-playback device by a media-delivery system based on a request for media content items that specifies the cadence.

13. A method of cadence-based media playback for use during repetitive-motion activities comprising:
determining a cadence associated with a repetitive motion activity based on acceleration data captured by a plurality of accelerometers, wherein the acceleration data comprises sequences of acceleration sample data captured from each of the plurality of accelerometers over a duration of time, by:
filtering the sequences of measurements based on frequency to generate filtered sequences;
identifying a signal corresponding to the cadence from the filtered sequences by combining the filtered sequences having a highest energy at each particular time interval;
calculating aggregate values corresponding to periods of oscillation of the filtered sequences over intervals during the duration of time; and
calculating a cadence value based on the aggregate values;
identifying a media content item based on the determined cadence; and
playing back the identified media content item.

14. The method of claim 13 further comprising:
smoothing the aggregate values to generate smoothed aggregate values;
determining whether the aggregate value and the smoothed aggregate value satisfy predetermined tolerances, wherein the predetermined tolerances include a difference tolerance and a duration requirement; and
upon determining that the predetermined tolerances are satisfied, calculating a cadence value based on the aggregate value.

15. The method of claim 13 further comprising:
monitoring the acceleration data captured by the plurality of accelerometers to detect changes in cadence; and
upon detecting a change in cadence identifying a second media content item based on the changed cadence and playing back the second media content item.

16. A method of cadence-based media playback for use during repetitive-motion activities comprising:
capturing acceleration data by a plurality of accelerometers over a duration of time, wherein the acceleration data comprises sequences of acceleration measurements captured at particular times throughout the duration by each of the accelerometers;
filtering each of the sequences of measurements based on frequency to generate filtered sequences;
identifying a cadence signal corresponding to the cadence from the filtered sequences, wherein the signal corresponding to the cadence is identified by combining the filtered sequences having a highest energy during subintervals of the duration;
calculating a sequence of first aggregate values corresponding to periods of oscillation of the cadence signal over intervals during the duration of time;
smoothing the sequence of first aggregate values to generate a sequence of second aggregate values;
determining whether the sequence of first aggregate values and the sequence of second aggregate values satisfy predetermined tolerances, wherein the predetermined tolerances include a difference tolerance and a duration requirement; and upon determining that the predetermined tolerances are satisfied, calculating an initial cadence value based on the sequence of first aggregate values.

\* \* \* \* \*